(12) United States Patent
Mejlhede et al.

(10) Patent No.: US 7,887,737 B2
(45) Date of Patent: *Feb. 15, 2011

(54) INJECTION MOULDING OF A CATHETER

(75) Inventors: Signe Thorning Mejlhede, Svinninge (DK); Steffen Gyrn, Ringsted (DK)

(73) Assignee: Unomedical, A/S, Birkeroed (DK)

( * ) Notice: Subject to any disclaimer, the term of this patent is extended or adjusted under 35 U.S.C. 154(b) by 946 days.

This patent is subject to a terminal disclaimer.

(21) Appl. No.: 10/578,972

(22) PCT Filed: Nov. 12, 2004

(86) PCT No.: PCT/DK2004/000787

§ 371 (c)(1), (2), (4) Date: Jan. 16, 2007

(87) PCT Pub. No.: WO2005/046959

PCT Pub. Date: May 26, 2005

(65) Prior Publication Data

US 2007/0224309 A1    Sep. 27, 2007

Related U.S. Application Data

(60) Provisional application No. 60/519,656, filed on Nov. 14, 2003.

(30) Foreign Application Priority Data

Nov. 14, 2003 (DK) ................................ 2003 01691

(51) Int. Cl.
  *B29C 45/26* (2006.01)

(52) U.S. Cl. .................................... 264/328.1; 264/334
(58) Field of Classification Search ............. 264/328.1, 264/334

See application file for complete search history.

(56) References Cited

U.S. PATENT DOCUMENTS

| | | | |
|---|---|---|---|
| 3,348,544 A | 10/1967 | Braun |
| 3,385,553 A | 5/1968 | Braun |
| 3,694,280 A | 9/1972 | Hoef |
| 4,360,024 A | 11/1982 | Wallace |
| 4,404,159 A | 9/1983 | McFarlane |

(Continued)

FOREIGN PATENT DOCUMENTS

EP    1 116 567    7/2001

(Continued)

OTHER PUBLICATIONS

International Search Report dated Feb. 7, 2005 for International Application No. PCT/DK2004/000787.

(Continued)

*Primary Examiner*—Jill L Heitbrink
(74) *Attorney, Agent, or Firm*—Brinks Hofer Gilson & Lione

(57) ABSTRACT

A method for producing a one-piece catheter comprising a hub (3) and a tube-shaped flexible part (4) wherein the tube shaped flexible part (4) has an interior which is divided in two region one being cone-shaped (7-8) and one being cylindrical (5). A one-piece catheter of the above mentioned kind and a mould for moulding such catheter.

10 Claims, 3 Drawing Sheets

U.S. PATENT DOCUMENTS

| | | | |
|---|---|---|---|
| 5,032,343 | A | 7/1991 | Jeffs et al. |
| 5,057,083 | A | 10/1991 | Gellman |
| 5,510,065 | A | 4/1996 | McFarlane |
| 5,522,803 | A | 6/1996 | Teissen-Simony |
| 6,630,086 | B1 | 10/2003 | Goral et al. |
| 6,767,496 | B1 | 7/2004 | Jensen et al. |
| 6,887,417 | B1 | 5/2005 | Gawreluk et al. |
| 7,431,876 | B2 * | 10/2008 | Mejlhede et al. ......... 264/328.1 |
| 2001/0009988 | A1 | 7/2001 | Kafrawy et al. |
| 2005/0033237 | A1 | 2/2005 | Fentress et al. |

FOREIGN PATENT DOCUMENTS

| | | |
|---|---|---|
| FR | 1 336 357 A | 8/1963 |
| GB | 819 225 | 9/1959 |
| GB | 2 230 702 A | 10/1990 |
| WO | WO 90/00960 | 2/1990 |
| WO | WO 90/00960 A1 | 2/1990 |
| WO | WO 03/026728 A1 | 4/2003 |
| WO | WO 03/039639 A2 | 5/2003 |

OTHER PUBLICATIONS

International Preliminary Report on Patentability dated Mar. 8, 2006 for International Application No. PCT/DK2004/000787.
Menges, Georg et al.; "How to Make Injection Molds"; $3^{rd}$ edition; Hanser Publishers; 2001; pp. 401-420.
Office Action mailed Feb. 24, 2006 for U.S. Appl. No. 10/712,260.
Office Action mailed Jul. 27, 2006 for U.S. Appl. No. 10/712,260.
Office Action mailed Feb. 14, 2007 for U.S. Appl. No. 10/712,260.
Advisory Action mailed Jul. 26, 2007 for U.S. Appl. No. 10/712,260.
Office Action mailed Sep. 13, 2007 for U.S. Appl. No. 10/712,260.

* cited by examiner (10)

INJECTION MOULDING OF A CATHETER

This application is the National Stage of International Application No. PCT/DK2004/000787, filed Nov. 12, 2004, which claims priority to Danish Application No. PA 2003 01691 filed Nov. 14, 2003, U.S. Provisional Application No. 60/519,656 filed Nov. 14, 2003, and U.S. application Ser. No. 10/712,260 filed Nov. 14, 2003. These references are incorporated herein in their entirety.

FIELD OF INVENTION

The present invention relates to catheters and an improved method of producing such catheters.

BACKGROUND

In general a catheter is a device for transporting a fluid to or from a body cavity. Often catheters comprise a tube-shaped part which facilitates the fluid transport.

A subgroup of catheters is known as soft needle catheters and they have a wide range of applications, e.g. in automated drug delivery devices such as insulin delivery devices. The soft needle catheters are in general more flexible and softer than other catheters.

The soft needle catheters are generally used together with an introducer needle, where the needle is used to penetrate the barrier to the body e.g. the skin and assist the introduction of the catheter. The needle is removed after introduction of the catheter into a body cavity. The soft needle catheter is left in the body cavity for a desired period of time in which it functions as the means for drug delivery. The soft needle catheter is removed from the body cavity, by simple withdrawing after end of use.

A soft needle catheter often comprises a tube-shaped flexible part and a hub. The tube-shaped flexible part is adapted for insertion into a patient and it facilitates the fluid transport to or from a body cavity. The tube-shaped part must be flexible in order to allow the carrier of the catheter, e.g. a patient, to move without serious unpleasantness. However it must not be so flexible that it is capable of forming kinks which may stop the drug delivery. The hub is the connecting means on the tube shaped part adapted for connecting the tube shaped part to either the drug delivery devise, to the fluid collecting container or to another connecting means e.g. a second tube.

Soft needle catheters can be manufactured as one-piece catheters or two-piece catheters, where the tube-shaped part and the hub are made separately. A two piece catheter is easier to manufacture but it suffers from the drawback that there is a risk of separation, especially during removal of the catheter, leaving the tube-shaped part in the body cavity. Therefore one-piece soft needle catheters are preferred.

Moulding of one-piece soft needle catheters is complicated due to the dimensions of the catheter. There is a risk that the tube-shaped part wrinkles during removal from the mould form either as a consequence of the withdrawal of the core creating the hollow part or as a consequence of sticking to the mould.

Different approaches to the manufacture of one-piece soft catheters are known from the literature.

EP 1 116 567 A2 discloses a method using gas assisted injection moulding and a mould which splits perpendicular to the axis of the tube-shaped part, approximately on the middle. During moulding there is a risk that a fin forms at the splitting line of the mould. A fin placed at the middle of the tube-shaped part might cause unnecessary pain or even cuts to a patient during penetrations of the skin.

GB 819 225 discloses a method for injection moulding of a silicone rubber self-retaining catheter adapted to receive a stopper, where a wire is used as the moulding core.

WO 90/00960 discloses a method of producing soft needle catheters in which a sleeve is mounted on the core of the mould. The sleeve assists the removal of the core after curing. Use of sleeves complicates the production and increases the production costs.

Therefore it is desirable to have a new method for production of soft needle catheters which can avoid the drawbacks of the prior art.

SUMMARY OF THE INVENTION

It has been discovered that by extending the cone-shaped part of the core for creating the interior of the soft needle catheter, from the hub and further into the tube-shaped part, it is possible to remove the core after moulding without wrinkling of the tube-shaped part. Therefore it is now possible to mould soft needle catheters without the assistance of gas and/or sleeves. This makes the production process cheaper and simpler.

According to the invention there is provided a method for one piece injection moulding of a soft needle catheter comprising a hub and a tube-shaped flexible part, comprising the steps of:

feeding a molten polymer into a mould comprising a core which together define a hub cavity and a tube-shaped cavity, said core having a cone-shaped part within the hub cavity and a cylindrical part, said core being used to form the interior of the catheter;

removing the core form the catheter when the polymer has been sufficiently cured for the core to be removed; and removing the catheter from the mould when the polymer has been sufficiently cured to be removed;

which is characterized in using a core wherein the cone-shaped part of the core extends into the tube-shaped cavity.

In a preferred embodiment the core is cylindrical at the tip resulting in a cylindrical tip of the tube-shaped part of the catheter.

Further there is provided a new soft needled catheter comprising a hub and a tube-shaped flexible part, wherein the interior i.e. the lumen of the tube-shaped part both has a cone-shaped part ("the cone-shaped part") and a cylindrical part ("the cylindrical part").

Even further there is provided a mould comprising a hub cavity, a tube-shaped cavity and a core having a cone-shaped part and a cylindrical part being characterized in that the cone-shaped part of the core extends into the tube-shaped cavity.

Another aspect of the invention relates to a method for one-piece injection moulding of a soft needle catheter comprising a hub and a tube-shaped flexible part, comprising the steps of:

feeding a molten polymer into a mould comprising a core which together define a cavity composed of a hub cavity and a tube-shaped cavity, said core having a cone-shaped part and a cylindrical part, said core being used to form the interior of the catheter;

removing the core from the catheter when the polymer has been sufficiently cured for the core to be removed; and removing the catheter from the mould when the polymer has been sufficiently cured to be removed;

characterized in using a core wherein the cone-shaped part of the core forms at least a part of the interior of the hub and extends into the tube-shaped cavity so as to form an interior of the tube-shaped flexible part being at least partially cone shaped.

In a preferred embodiment the core has a cylindrical shape at the tip thus resulting in a cylindrical interior of the tube shaped part at the tip.

DESCRIPTION OF PREFERRED EMBODIMENTS

Figure 1:
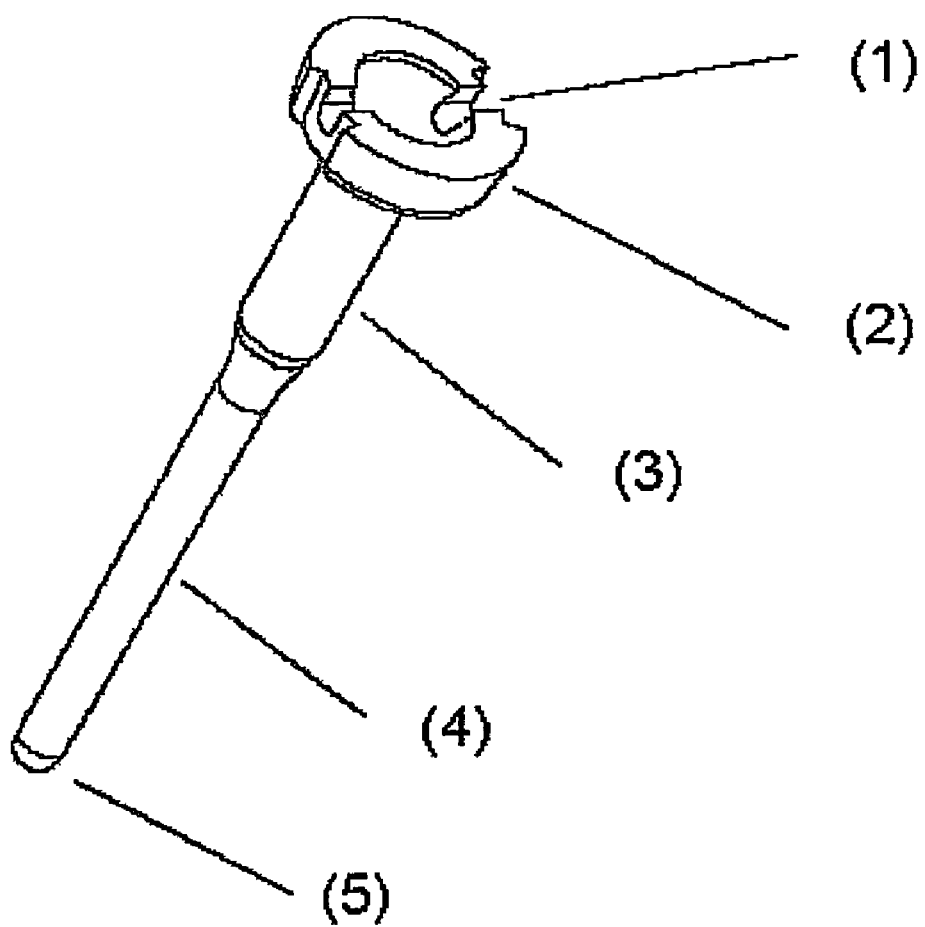
FIG. 1 shows a preferred embodiment of the soft needle catheter according to the invention.

In the method according to the invention the molten polymer is fed into a mould comprising a hub cavity, a tube-shaped cavity and a core having a cone-shaped part and a cylindrical part, where said cone-shaped part of the core is located in the part of the mould form creating the hub cavity and where the cone is extending into the tube-shaped cavity. After curing the core is removed from the catheter and the catheter is removed from the mould or visa versa.

Optionally the soft needle catheter can be cured to the final state after removal from the mould.

The core with the cone-shaped part and the cylindrical part creates a cone-shaped part and a cylindrical part of the lumen of the tube-shaped part of the catheter.

The cone-shaped part of the core eases the release of the core whereas the cylindrical part creates an area with the frictional resistance which is desired during the insertion.

In a preferred embodiment, the material is supplied to the mould via at least two inlets thereby minimizing the risk of tilting the core. It is preferred to place the inlets symmetrically around the axis of the core. This further aids in centering the core thereby creating walls of essentially equal thickness.

Preferably the inlets are placed at the hub forming part of the mould hereby placing possible polymer surplus at the non-skin penetrating part of the catheter, more preferably the inlets are placed at rim of the hub.

In a preferred embodiment of the invention the mould separates along the axis of the tube part (4) of the catheter to be moulded. By separating along this axis it is possible to achieve sufficient force (thrust load) on the mould to avoid creation of fins.

In another preferred embodiment of the invention the mould is separated perpendicular to the axis of the tube (4) of the catheter to be moulded, but at the hub or just below the hub. If a fin is created, then it will appear on the part of the soft needle catheter which does not penetrate the skin and thereby avoiding possible unpleasantly.

Preferably soft needle catheters are composed of a material which are sufficiently flexible to bend, when the carrier moves and sufficiently rigid to avoid kinking closing off the drug supply. Further the material must be compatible with medical use i.e. irritation of the skin must be kept at a minimum, being non-toxic it must not decompose in the body, etc. Thermoplastic elastomers (TPE) are a type of material which fulfils these requirements. Examples of such useful elastomers are: polyester ethers, ECDEL, styrene based TPE, olefin based TPE, urethane based TPE, ester based TPE, amid based TPE, polyolefines and silicone rubbers. In a preferred embodiment the material is selected from the group consisting of polypropylene, C-FLEX™, mixtures of C-FLEX™ and polypropylene, LUPOLEN™ 1840H, LUPOLEN™ 3020D, PELLETHANE™ 2363-75D, PELLETHANE™ 2363-55D, TECOTHANE™ and CARBOTHANE™.

In another preferred embodiment the materials is selected from the group consisting of PTFE, PP and PE-LD.

Preferably the materials should have a shore in the range of 40-60D but as the skilled person knows flexibility is a function of the thickness of the walls also. Therefore the chosen shore will depend on the wall thickness.

Optionally more than one polymer is used in the moulding either as a mixture or in an embodiment where one part of the catheter essentially comprises a first polymer and another part of the catheter essentially comprises a second polymer.

Preferred materials are required to pass all the four following tests:

| Test | Definition/execution |
| --- | --- |
| Introduction force | Introduction force is tested by LLOYD tensile strength apparatus is used. |
| Peelback | Peelback means sliding of the soft needle catheter on the needle by insertion. |
| Kink-angle | The angle at which the soft needle catheter kinks, preferably as large as possible |
| Tensile strength | Drawing until the catheter breaks |

Preferred materials further fulfil the following requirements:

ISO 10993-1/USP class VI

The material is able to withstand sterilization e.g. ETO

The material is drug compatible e.g. insulin compatible

By the new method of injection moulding of catheters a new type of catheters is provided. These new catheters have a tube-shaped part with a lumen which is divided into a region being cone-shaped (the cone-shaped part) and region being a cylindrical interior (the cylindrical part).

In a preferred embodiment the lumen of tube-shaped part of the soft needle catheter has a ratio between length of the cylindrical part and length of the cone-shaped part in the range from 10:1 to 1:40, preferably the range is from 5:1 to 1:30, more preferably the range is from 2:1 to 1:20 and most preferably from 1:1 to 1:15. In an even more preferred embodiment the range is determined by the maximum length of the cylindrical part of the lumen which does not create wrinkling when the core is removed and which fulfils the requirement of skin penetration and removal to the introduction needle. A suitable length of the cylindrical part is 1.5 mm.

The combination of a cone-shaped interior and a cylindrical interior of the tube-shaped part provides the manufacturer with soft needle catheters with an increased choice of materials. A friction between the needle and the soft needle catheter substantially arises from the cylindrical part of the tube. By shortening or lengthening the extension of the cylindrical part it is possible to achieve desired peal and/or introduction forces with materials which otherwise could not have been used.

The cylindrical part of lumen of the tube provides the tight closure between the needle and the soft needle catheter which is essential during the injection of the catheter. Preferably the cylindrical part is placed at the outlet of the tube-shaped part (the opposite end of the tube than the hub).

In principle the catheter can be of any length as long as it does not wrinkle during moulding, but it is preferred that the length of the tube part of the soft needle catheters is less than 50 mm, more preferably less than 25 mm, even more preferably between 5 mm and 15 mm, most preferred is the range between 7 mm to 10 mm.

In a preferred embodiment the wall part of the tube with cylindrical lumen has a thickness between 0.01 mm and 0.5 mm, preferably between 0.05 mm and 0.3 mm and most preferred between 0.09 mm and 0.1 mm.

In a preferred embodiment the cylindrically shaped part of the tube-shaped part has an outer diameter between 0.3 mm and 1.3 mm In a preferred embodiment the cylindrically shaped part of the tube-shaped part has an inner diameter between 0.2 mm and 1.2 mm.

In a preferred embodiment the wall cone shaped part of the tube-shaped part has a thickness between 0.01 mm and 0.5 mm, preferably between 0.05 mm and 0.3 mm and most preferred between 0.09 mm and 0.1 mm.

In a preferred embodiment the walls of the hub, the cone-shaped part of the tube-shaped part and the cylindrical part of the tube-shaped part all have different thicknesses.

In a preferred embodiment the cone-shaped part of the catheter has a maximum outer diameter between 0.5 mm and 1.3 mm and a minimum outer diameter between 0.3 mm and 0.4 mm depending on the length of the catheter.

In a preferred embodiment the walls of the cone-shaped part of the tube has the same thickness in the entire cone-shaped region.

In a preferred embodiment the hub is fitted with means for assisting the removal of the soft needle catheter from the patient. Examples of such means are a flap, a rim and a groove. It is not intended to limit the assisting means to those listed above.

In a preferred embodiment the hub is further fitted with at least one carving, more preferably two carvings placed opposing each other, allowing drug inlet.

In a preferred embodiment the hub has means for sealing the soft needle catheter to a drug delivery device. The means can be provided on the outside of the hub in form of at least one round going packing, rim or fin or it can be by having a hub with a cone shaped exterior having a size suitable to fit into a cone shaped cavity of a drug delivery device.

In another preferred embodiment the hub both has a cone shaped exterior and additional means for sealing the soft needle catheter to the drug delivery device e.g. the previously mentioned packing, rim or fin.

Figure 3:
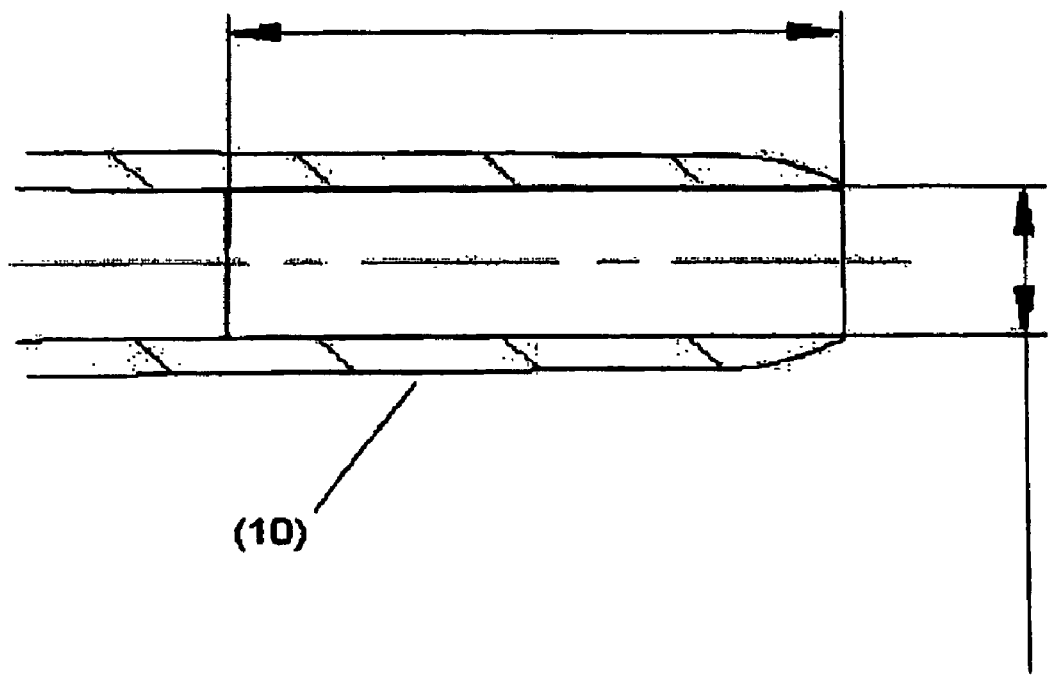
FIG. 3 shows a preferred embodiment of the cylindrical part of the catheter's tube part.

In a preferred embodiment the soft needle catheters have a rounding at the end in order to make the introduction into the subject less painful. In a more preferred embodiment the rounding is limited to the outer 1.5 mm as shown in FIG. 3.

In a preferred embodiment the soft needle catheter has an introduction force which allows it to stay firm on the introduction needle while being introduced into the body cavity and which allows the introduction needle to be withdrawn after introduction without wrinkling the tube-shaped part.

In another preferred embodiment the soft needle catheters are composed of more than one type of material e.g. the tube part is made of one material and the hub part of another. In this embodiment the moulding is however still one-piece moulding. This can be achieved by first adding one material to the mould and then a second material or it can be achieved by letting different inlets supply different materials.

In a preferred embodiment intended for use in infusion devices such as infusion devices describes in U.S. Pat. No. 5,522,803 and PCT/DK02/00640 and the preferred drug is insulin.

Example 1

Three selected materials, LDPE Lupolen 3020D, LDPE Lupolen 1840H and Hostaform MT24U01 were tested according to the described methods. The results are listed below:

| Test | LDPE Lupolen 3020D | LDPE Lupolen 1840H | Hostaform MT24U01 |
| --- | --- | --- | --- |
| Introduction force | Approved | Approved | Approved |
| Peelback | Approved | Approved | Approved |
| Kink-angle | Approved | Not-approved | — |
| Tensile strength | Approved | Approved | Approved |
| General opinion | Usable material - acceptably bendable and soft - but lacks the elastic element | Usable material - acceptably bendable and soft - but lacks the elastic element | Very hard material |

Example 2

Figure 2:
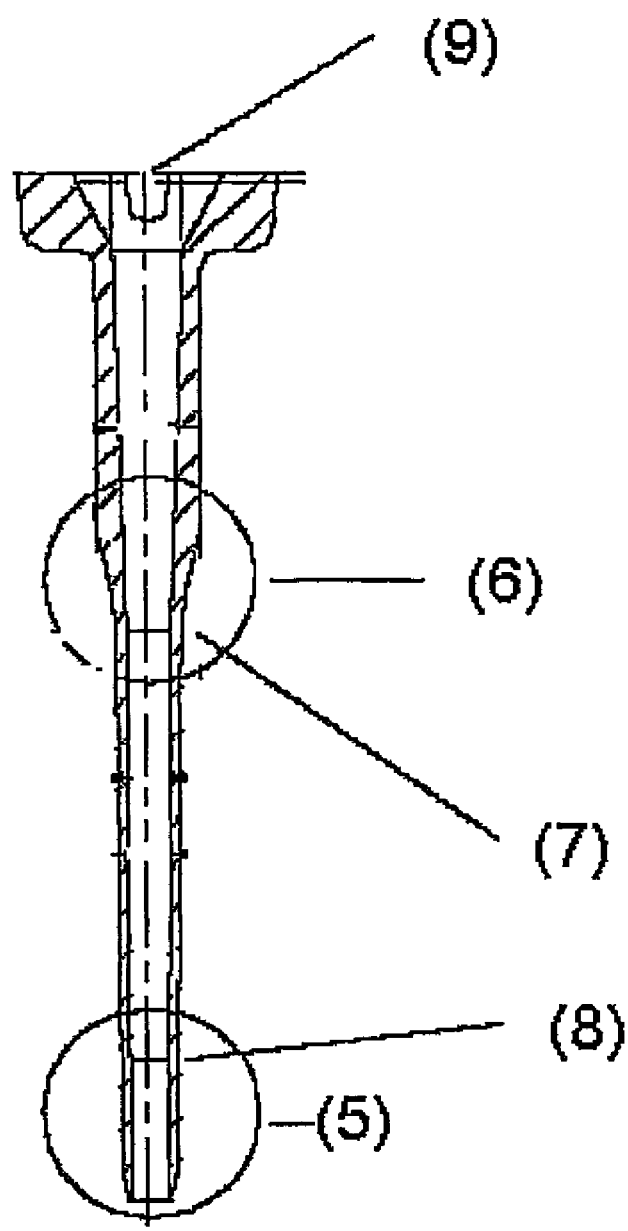
FIG. 2 shows a cross sectional view of a preferred embodiment of the soft needle catheter according to the invention.

In FIG. 1 a preferred soft needle catheter according to the invention is shown. The catheter comprises a hub (3) and a tube-shaped part (4). The hub further comprises a rim (2) having a carving (1). The tube-shaped part is rounded at the cylindrical part (5) of the tube-shaped part. FIG. 2 shows the preferred soft needle catheter according to the invention in a cross sectional view. It can be seen that the hub decreases its diameter in a zone (6) until it has the same diameter as the tube-shaped part which begins at (7). The tube-shaped part has a cone-shaped part extending from (7) to (8) and a cylindrical part (5). Further it can be seen that the core (9) has a cone-shaped part extending into the tube-shaped part (from the top to (8)) and a cylindrical part (from (8) and the rest of the core)). FIG. 3 shows an enlargement of the cylindrical part of tube-shaped part. In this embodiment is seen how the cylindrical part is rounded (10) and has the dimension 1.5 mm long and with an inner diameter of 0.4 mm.

The catheter can be used intravenously or subcutaneously, preferably for intravenous or subcutaneous injection of a drug.

The invention claimed is:

1. A method for one-piece injection moulding of a soft needle catheter used together with an introducer needle comprising a hub and a tube-shaped flexible part, comprising the steps of:
   feeding a molten polymer into a mould comprising a core defining a cavity comprising a hub cavity and a tube-shaped cavity, said core having a cone-shaped part and a cylindrical part forming the interior of the catheter;
   removing the core from the catheter; and
   removing the catheter from the mould;
   wherein the cone-shaped part of the core forms at least a part of the hub cavity and extends into the tube-shaped cavity causing the interior of the tube-shaped flexible part to be at least partially cone shaped.

2. A method according to claim 1, wherein the catheter is cured to its final state in the mould.

3. A method according to claim 1, wherein the molten polymer is supplied to the mould via at least two inlets.

4. A method according to claim 1, wherein the inlets are placed at the hub forming part of the mould.

5. A method according to claim 1, wherein the mould separates along the axis of the tube-shaped part.

6. A method according to claim 1, wherein the mould separates perpendicular to the tube-shaped part and at or just below the hub.

7. A method according to claim 1, wherein the polymer is chosen from polyester ethers, styrene based TPE, olefin based TPE, urethane based TPE, ester based TPE, amid based TPE polyolefines and silicone rubbers.

8. A method according to claim 1, wherein the polymer has a shore between 40 and 60D.

9. A method according to claim 1, wherein a plurality of polymers are used.

10. The method of claim 3, wherein the inlets are placed symmetrically around the axis of the core.

* * * * *